US011185509B2

(12) United States Patent
Takaki et al.

(10) Patent No.: US 11,185,509 B2
(45) Date of Patent: Nov. 30, 2021

(54) SOLID PREPARATION HAVING IMPROVED LIGHT STABILITY

(71) Applicant: Toray Industries, Inc., Tokyo (JP)

(72) Inventors: Suguru Takaki, Kamakura (JP); Satoshi Minakami, Kamakura (JP); Kotoe Ohta, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 37 days.

(21) Appl. No.: 16/320,429

(22) PCT Filed: Jul. 28, 2017

(86) PCT No.: PCT/JP2017/027391
§ 371 (c)(1),
(2) Date: Jan. 24, 2019

(87) PCT Pub. No.: WO2018/021518
PCT Pub. Date: Feb. 1, 2018

(65) Prior Publication Data
US 2019/0262270 A1  Aug. 29, 2019

(30) Foreign Application Priority Data
Jul. 29, 2016  (JP) .............................. JP2016-150238

(51) Int. Cl.
| | |
|---|---|
| *A61K 9/20* | (2006.01) |
| *A61K 31/485* | (2006.01) |
| *A61K 9/48* | (2006.01) |
| *A61K 9/14* | (2006.01) |
| *A61K 47/10* | (2017.01) |
| *A61K 9/16* | (2006.01) |
| *A61K 47/02* | (2006.01) |
| *A61K 47/08* | (2006.01) |
| *A61K 47/22* | (2006.01) |
| *A61K 47/26* | (2006.01) |
| *A61P 17/04* | (2006.01) |

(52) U.S. Cl.
CPC .............. *A61K 9/2013* (2013.01); *A61K 9/14* (2013.01); *A61K 9/16* (2013.01); *A61K 9/20* (2013.01); *A61K 9/2009* (2013.01); *A61K 9/2018* (2013.01); *A61K 9/2054* (2013.01); *A61K 9/48* (2013.01); *A61K 31/485* (2013.01); *A61K 47/02* (2013.01); *A61K 47/08* (2013.01); *A61K 47/10* (2013.01); *A61K 47/22* (2013.01); *A61K 47/26* (2013.01); *A61P 17/04* (2018.01)

(58) Field of Classification Search
CPC ........ A61K 31/44; A61K 31/485; A61K 9/14; A61K 9/16; A61K 9/20; A61K 9/48
See application file for complete search history.

(56) References Cited

U.S. PATENT DOCUMENTS

| | | | |
|---|---|---|---|
| 6,372,755 B2 * | 4/2002 | Hanamura | A61P 25/04 |
| | | | 514/282 |
| 2001/0004637 A1 | 6/2001 | Hanamura et al. | |
| 2010/0120815 A1 | 5/2010 | Takaki et al. | |
| 2012/0058186 A1 * | 3/2012 | Takaki | A61K 31/18 |
| | | | 424/482 |

FOREIGN PATENT DOCUMENTS

| | | |
|---|---|---|
| EP | 2356989 A1 | 8/2011 |
| JP | 58-57322 A | 4/1983 |
| JP | 2005-2123 A | 1/2005 |
| JP | 2006-306754 A | 11/2006 |
| JP | 2015-168630 A | 9/2015 |
| JP | 2015168630 A * | 9/2015 |
| JP | 2015-172043 A | 10/2015 |
| JP | 2015-172053 A | 10/2015 |
| JP | 2015172043 A * | 10/2015 |
| WO | 99/02158 A1 | 1/1999 |
| WO | 2008/133330 A1 | 11/2008 |
| WO | 2010/113841 A1 | 10/2010 |
| WO | 2016/052617 A1 | 4/2016 |
| WO | 2016/195057 A1 | 12/2016 |

OTHER PUBLICATIONS

Inui et al (Clinical Cosmetic Investig Dermatol. vol. 11 pp. 249-255. Published 2015) (Year: 2015).*
Reich et al. (Chapter 11: Formulation and physical properties of soft capsules, Pharmaceutical Capsules 2nd Edition, Pharmaceutical Press pp. 201-212, published 2004) (Year: 2004).*
The Extended European Search Report dated Feb. 11, 2020, of counterpart European Application No. 17834520.3.

* cited by examiner

*Primary Examiner* — Theodore R. Howell
*Assistant Examiner* — George W Kosturko
(74) *Attorney, Agent, or Firm* — DLA Piper LLP (US)

(57) ABSTRACT

A solid preparation includes a 4,5-epoxymorphinan derivative or a pharmaceutically acceptable acid addition salt thereof, which is stable to light even without light shielding coating. The solid preparation includes an active ingredient composed of a 4,5-epoxymorphinan derivative or a pharmaceutically acceptable acid addition salt thereof, and one or more stabilizing agents selected from the group consisting of n-propyl gallate, sodium hydrogensulfite, dibutylhydroxytoluene, butylhydroxyanisole, tocopherol and D-isoascorbic acid, wherein the amount of the above active ingredient is 0.00001 to 0.01% by weight of the solid preparation, and the amount of the above stabilizing agent is 0.005 to 5% by weight of the solid preparation.

6 Claims, No Drawings

SOLID PREPARATION HAVING IMPROVED LIGHT STABILITY

TECHNICAL FIELD

This disclosure relates to a solid preparation with improved photostability, which comprises a 4,5-epoxymorphinan derivative or a pharmaceutically acceptable acid addition salt thereof.

BACKGROUND

Nalfurafine and pharmaceutically acceptable acid addition salts thereof, which are known to be compounds with remarkable antipruritic effects, are chemically unstable to, for example, heat, light, and oxygen. Thus, a method of improving the chemical stability thereof has been conventionally developed.

Specifically, a method in which a substance selected from particular antioxidants, synergists, saccharides and surfactants is added, and a method in which sodium thiosulfate, saccharides, or sugar alcohols and low substituted hydroxypropyl cellulose are added have been reported (WO 99/002158 and WO 08/133330).

The preparation described in WO 99/002158 contains a substance selected from particular antioxidants, synergists, saccharides and surfactants to improve the stability of nalfurafine or a pharmaceutically acceptable acid addition salt thereof, and tablets and granules are described as specific dosage forms for the solid preparation. Additionally, the solid preparation described in WO 08/133330 contains sodium thiosulfate, saccharides, or sugar alcohols and low substituted hydroxypropyl cellulose as stabilizing agents to improve the stability of nalfurafine or a pharmaceutically acceptable acid addition salt thereof.

In addition, a capsule filler composition prepared by adding a medium-chain fatty acid triglyceride and propyl gallate to a liquid filler for soft capsule preparations, and a soft capsule preparation containing a particular matrix and an antioxidant are reported as formulations to stabilize nalfurafine or a pharmaceutically acceptable acid addition salt thereof in soft capsule preparations (JP 2015-168630 A and JP 2015-172043 A).

Specifically, the soft capsule preparations described in JP 2015-168630 A and JP 2015-172043 A contain an antioxidant such as propyl gallate as a stabilizing agent to improve the stability of nalfurafine or a pharmaceutically acceptable acid addition salt thereof.

The orally disintegrating tablet described in WO 10/113841 ensures excellent photostability by applying a coating being composed of a polyvinyl alcohol-based resin and a particular saccharide and containing a light-shielding agent on an orally disintegrating tablet containing nalfurafine or a pharmaceutically acceptable acid addition salt thereof.

Meanwhile, a light-shielding coating agent containing a polyvinyl alcohol-based resin and a particular saccharide is reported as a formulation to improve the photostability of a drug unstable to light, which contains nalfurafine or a pharmaceutically acceptable acid addition salt thereof in solid preparations (WO 10/113841).

In addition, various methods to stabilize the drug unstable to light are known in relation to the formulation of those drugs. As methods to improve the photostability of amlodipine, which is unstable to light, in uncoated tablets, for example, a method in which ferric oxide is added, and a method in which a dissolved substance having the similar light absorption behavior to that of the active ingredient to be protected from light is added have been reported (JP 2006-306754 A and JP S58-57322 A).

The preparation described in JP 2006-306754 A is a preparation whose photostability is improved by combining amlodipine, which is unstable to light, with ferric oxide. In the method described in JP S58-57322 A to improve photostability, a dissolved substance having the similar light absorption behavior to that of the active ingredient to be protected from light is added to improve photostability.

However, no study is conducted in WO 99/002158 on the improvement of the photostability of nalfurafine or a pharmaceutically acceptable acid addition salt thereof, though an improvement in heat and oxidation stability has been indicated by data.

Also, no study is conducted in WO 08/133330 on the improvement of the photostability of nalfurafine or a pharmaceutically acceptable acid addition salt thereof though an improvement in heat and oxidation stability has been indicated by data, and only a commonly used light shielding coating for tablets is applied.

In JP 2015-168630 A and JP 2015-172043 A, the stability thereof against heat and oxidation during storage is indicated by data, but there is neither a description nor suggestion on the improvement of photostability.

As seen above, the techniques described in WO 99/002158, WO 08/133330, JP 2015-168630 A and JP 2015-172043 A to stabilize nalfurafine or a pharmaceutically acceptable acid addition salt thereof are methods for stabilization of preparations during production and/or long-term storage, and no study has been conducted on the improvement of photo stability.

When the orally disintegrating tablet described in WO 10/113841 is split for proper dosing, an uncoated surface appears in each split surface of the tablet and deterioration of the tablet such as degradation or color change due to exposure to light may proceed from the uncoated surfaces. A large amount of coating is required to ensure sufficient photostability for solid preparations in powder or granule form, which may result in decreased stability during production and/or long-term storage or may cause the production process to be complicated.

For the preparation described in JP 2006-306754 A, addition of butylhydroxyanisole and dibutylhydroxytoluene as stabilizing agents to inhibit oxidative degradation is described. JP 2006-306754 A describes that these antioxidants reduce the production of degradation products from amlodipine due to its oxidation, but do not inhibit color change at all.

In the method described in JP S58-57322 A to improve photostability, there is no description on nalfurafine or a pharmaceutically acceptable acid addition salt thereof, and different methods to improve photostability are effective for different active ingredients.

Thus, it could be helpful to provide a solid preparation comprising a 4,5-epoxymorphinan derivative or a pharmaceutically acceptable acid addition salt thereof, which is stable to light even without light shielding coating.

SUMMARY

We thus Provide:

(1) A solid preparation comprising an active ingredient composed of a 4,5-epoxymorphinan derivative represented by general formula (I) below or a pharmaceutically acceptable acid addition salt thereof, and one or more stabilizing agents selected from the group consisting of n-propyl gallate, sodium hydrogensulfite, dibutylhydroxytoluene, butylhydroxyanisole, tocopherol and D-isoascorbic acid, wherein the amount of the above active ingredient is 0.00001 to 0.01% by weight of the solid preparation, and the amount of the above stabilizing agent is 0.005 to 5% by weight of the solid preparation

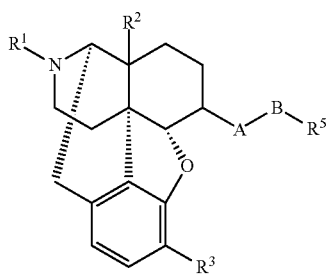

(I)

wherein $R^1$ represents cyclopropylmethyl or allyl; $R^2$ represents hydrogen, hydroxy, acetoxy, or methoxy; $R^3$ represents hydrogen, hydroxy, acetoxy, or methoxy; A represents —N($R^4$)C(=O)— or —N($R^4$)C(=O)O—; $R^4$ represents hydrogen or a $C_{1-5}$ linear or branched alkyl; B represents a $C_{1-3}$ linear alkylene, —CH=CH—, or —C≡C—; $R^5$ represents hydrogen, phenyl, furyl, or thienyl, provided that a hydrogen(s) in the above phenyl, the above furyl and the above thienyl is/are optionally substituted with one or more groups selected from the group consisting of $C_{1-5}$ alkyl, $C_{1-5}$ alkoxy, $C_{1-5}$ alkanoyloxy, hydroxy, fluorine, chlorine, bromine, iodine, amino, nitro, cyano, isothiocyanato, trifluoromethyl, trifluoromethoxy and methylenedioxy.

(2) The solid preparation according to (1), wherein the stabilizing agent is n-propyl gallate.
(3) The solid preparation according to (1) or (2), which contains sodium thiosulfate.
(4) The solid preparation according to any of (1) to (3), which contains yellow ferric oxide, red ferric oxide, or black iron oxide.
(5) The solid preparation according to any of (1) to (4), which contains a carbohydrate.
(6) The solid preparation according to any of (1) to (5), which is in a dosage form selected from the group consisting of tablet, granule, fine granule, hard capsule, dry syrup, powder, pill and troche.
(7) A solid preparation comprising an active ingredient composed of a 4,5-epoxymorphinan derivative represented by general formula (I) below or a pharmaceutically acceptable acid addition salt thereof, a carbohydrate, and one or more stabilizing agents selected from the group consisting of n-propyl gallate, sodium hydrogensulfite, dibutylhydroxytoluene, butylhydroxyanisole, tocopherol and D-isoascorbic acid, wherein the amount of the above active ingredient is 0.00001 to 0.01% by weight of the solid preparation, and the amount of the above stabilizing agent is 0.005 to 5% by weight of the solid preparation

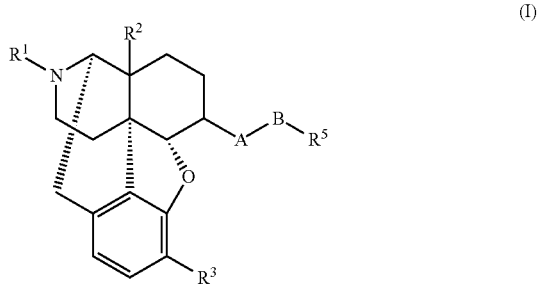

(I)

wherein $R^1$ represents cyclopropylmethyl or allyl; $R^2$ represents hydrogen, hydroxy, acetoxy, or methoxy; $R^3$ represents hydrogen, hydroxy, acetoxy, or methoxy; A represents —N($R^4$)C(=O)— or —N($R^4$)C(=O)O—; $R^4$ represents hydrogen or a $C_{1-5}$ linear or branched alkyl; B represents a $C_{1-3}$ linear alkylene, —CH=CH—, or —C≡C—; $R^5$ represents hydrogen, phenyl, furyl, or thienyl, provided that a hydrogen(s) in the above phenyl, the above furyl and the above thienyl is/are optionally substituted with one or more groups selected from the group consisting of $C_{1-5}$ alkyl, $C_{1-5}$ alkoxy, $C_{1-5}$ alkanoyloxy, hydroxy, fluorine, chlorine, bromine, iodine, amino, nitro, cyano, isothiocyanato, trifluoromethyl, trifluoromethoxy and methylenedioxy.

(8) The solid preparation according to (7), wherein the above stabilizing agent is n-propyl gallate.
(9) The solid preparation according to (7) or (8), which contains sodium thiosulfate.
(10) The solid preparation according to any of (7) to (9), which contains yellow ferric oxide, red ferric oxide, or black iron oxide.
(11) The solid preparation according to any of (7) to (10), which is in a dosage form selected from the group consisting of tablet, granule, fine granule, hard capsule, dry syrup, powder, pill and troche.

The photostability of a solid preparation containing a 4,5-epoxymorphinan derivative or a pharmaceutically acceptable acid addition salt thereof is improved, which can increase the usefulness of the solid preparation as a pharmaceutical product.

DETAILED DESCRIPTION

Our solid preparations will now be described. However, this disclosure is not limited to the following examples. Unless otherwise clearly indicated, the symbol "%" refers to "% by weight".

The solid preparation is a pharmaceutical product containing an active ingredient formulated as a solid, and examples of the solid preparation include tablets (including sublingual tablets, orally disintegrating tablets and minitablets), hard capsules, granules, fine granules, powders, dry syrups, pills, troches and film preparations. In particular, we conveniently allow tablets to ensure photostability without forming a light-shielding coating film layer and thus disintegrate quickly in an oral cavity when the preparation is applied to orally disintegrating tablets. Additionally, we also conveniently ensure photostability without following a complex production process to form a uniform coating film layer containing a light-shielding agent on the outer surface of solid preparations in powder form when the preparation is applied to granules, fine granules, powders, dry syrups and film preparations.

The active ingredient is a 4,5-epoxymorphinan derivative represented by general formula (I) below or a pharmaceutically acceptable acid addition salt thereof.

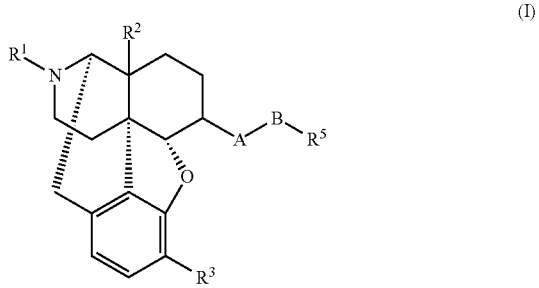

(I)

wherein $R^1$ represents cyclopropylmethyl or allyl; $R^2$ represents hydrogen, hydroxy, acetoxy, or methoxy; $R^3$ represents hydrogen, hydroxy, acetoxy, or methoxy; A represents —N($R^4$)C(=O)— or —N($R^4$)C(=O)O—; $R^4$ represents hydrogen or a $C_{1-5}$ linear or branched alkyl; B represents a $C_{1-3}$ linear alkylene, —CH=CH—, or —C≡C—; $R^5$ represents hydrogen, phenyl, furyl, or thienyl, provided that a hydrogen(s) in the above phenyl, the above furyl and the above thienyl is/are optionally substituted with one or more groups selected from the group consisting of $C_{1-5}$ alkyl, $C_{1-5}$ alkoxy, $C_{1-5}$ alkanoyloxy, hydroxy, fluorine, chlorine, bromine, iodine, amino, nitro, cyano, isothiocyanato, trifluoromethyl, trifluoromethoxy and methylenedioxy.

The hydrochloride salt of the compound represented by general formula (II) below, which is 17-(cyclopropylmethyl)-3,14β-dihydroxy-4,5α-epoxy-6β-[N-methyl-trans-3-(3-furyl)acrylamide]morphinan (hereinafter referred to as "nalfurafine"), is particularly preferred as the above 4,5-epoxymorphinan derivative represented by general formula (I) or a pharmaceutically acceptable salt thereof.

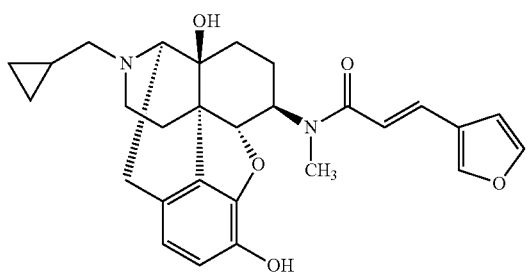

(II)

Examples of the pharmaceutically acceptable acid addition salt include inorganic acid salts such as hydrochloride, sulfate, nitrate, hydrobromide, hydroiodide, and phosphate; organic carboxylates such as acetate, lactate, citrate, oxalate, glutarate, malate, tartrate, fumarate, mandelate, maleate, benzoate, and phthalate; organic sulfonates such as methanesulfonate, ethanesulfonate, benzenesulfonate, p-toluenesulfonate, and camphorsulfonate. Among those, the hydrochloride, hydrobromide, phosphate, tartrate, maleate, and methanesulfonate are preferred; the hydrochloride which is commercially available is most preferred.

The amount of the active ingredient, which is the above 4,5-epoxymorphinan derivative represented by general formula (I) or a pharmaceutically acceptable acid addition salt thereof, is preferably 0.00001 to 0.01% by weight, more preferably 0.00005 to 0.01% by weight, further preferably 0.00025 to 0.01% by weight, of the solid preparation. When the amount of the active ingredient is more than 0.01% by weight, a solid preparation with sufficient photostability is obtained without using a stabilizing agent. When the amount of the active ingredient is less than 0.00001% by weight, a larger dose of the preparation is required to attain therapeutic effects.

The content range of the active ingredient in percent by weight varies depending on the amount of the solid preparation, and the active ingredient in an amount of 0.01 μg to 50 μg is typically contained in a daily dose of the solid preparation.

One or more stabilizing agents selected from the group consisting of n-propyl gallate, sodium hydrogensulfite, dibutylhydroxytoluene, butylhydroxyanisole, tocopherol and D-isoascorbic acid are used. Preferably n-propyl gallate and/or tocopherol, more preferably n-propyl gallate, are/is used as a stabilizing agent(s).

Commercially available products may be used as the stabilizing agents. n-Propyl gallate is commercially available under various names such as propyl gallate, gallic acid propyl ester, and 3,4,5-trihydroxybenzoic acid propyl ester. Dibutylhydroxytoluene is commercially available under various names such as BHT, 2,6-di-tert-butyl-p-cresol, 3,5-di-tert-butyl-4-hydroxytoluene, and 2,6-di-tert-butyl-4-methylphenol. Butylhydroxyanisole is commercially available under various names such as BHA, 3-t-butyl-4-hydroxyanisole, and tert-butyl-4-methoxyphenol. Tocopherol is commercially available under various names such as dl-α-tocopherol, d-α-tocopherol, d-δ-tocopherol, and vitamin E.

The amount of the stabilizing agent(s) is 0.005 to 5% by weight, preferably 0.005 to 1% by weight, of the solid preparation. When the amount of the stabilizing agent(s) is less than 0.005% by weight of the solid preparation, a sufficient photostabilizing effect is not obtained. When the amount of the stabilizing agent(s) is more than 5% by weight of the solid preparation, the amount is above the maximum daily dose of the stabilizing agent(s) which is confirmed to be safe, which amount is thus not preferred.

The solid preparation preferably further contains a carbohydrate. Examples of the carbohydrate include saccharides or sugar alcohols, and commercially available carbohydrates may be used. Examples of the carbohydrates include potato starch, sucrose, lactose, mannitol, erythritol, maltose, maltitol, trehalose, sorbitol, xylitol, lactitol and glucose, and the preferred are lactose, erythritol and mannitol. The use of a carbohydrate can improve the storage stability of the above 4,5-epoxymorphinan derivative represented by general formula (I) or a pharmaceutically acceptable acid addition salt thereof, as well as the sweetness of the carbohydrate improves drug compliance.

The solid preparation may further contain an antioxidant to prevent degradation of the active ingredient during production and/or long-term storage. Examples of such an antioxidant include sodium thiosulfate.

The solid preparation may contain various additives used in the production of common formulations, in addition to the above-described ingredients. Examples of such additives include excipients, disintegrators, binders, lubricants, coating agents, fluidizing agents, taste masking agents, flavoring agents, coloring agents and sweeteners.

Examples of the disintegrator include crospovidone, croscarmellose sodium, carmellose calcium, sodium carboxymethyl starch and low substituted hydroxypropyl cellulose.

Examples of the binder include water-soluble polysaccharides such as gelatin, pullulan, carrageenan, xanthan gum, tamarind gum, pectin, sodium alginate and gum arabic; celluloses such as hydroxypropyl cellulose, hydroxypropyl methylcellulose and methyl cellulose; starches such as alpha starch and gelatinized starch; and synthetic polymers such as polyvinylpyrrolidone, carboxy vinyl polymer and polyvinyl alcohol.

Examples of the lubricant include magnesium stearate, calcium stearate, sodium stearyl fumarate, talc, sucrose fatty acid esters, stearic acid, aluminium stearate, potassium sodium tartrate, light anhydrous silicic acid, carnauba wax, carmellose calcium, carmellose sodium, hydrated silicon dioxide, hydrogenated oil and hydrogenated rapeseed oil.

Examples of the coating agent include hydroxypropyl methylcellulose, ethyl cellulose, sodium carboxymethyl ethylcellulose and polyvinyl alcohol.

Examples of the fluidizing agent include talc, hydrated silicon dioxide and light anhydrous silicic acid.

Examples of the taste masking agent include glutamic acid, fumaric acid, succinic acid, citric acid, sodium citrate, tartaric acid, malic acid, ascorbic acid, sodium chloride and menthol.

Examples of the flavoring agent include orange, vanilla, strawberry, or yogurt flavorings and menthol.

Examples of the coloring agent include food colorants such as titanium oxide, ferric oxide, yellow ferric oxide, black iron oxide, talc, food red No. 3, food yellow No. 5 and food blue No. 1; and riboflavin.

Examples of the sweetener include aspartame, saccharin, dipotassium glycyrrhizinate and stevia.

The solid preparation can be manufactured by a wet granulation process comprising dissolving or suspending the active ingredient in water or a pharmaceutically acceptable solvent, and adding the obtained liquid (solution or suspension) to a carbohydrate. Additionally, the stabilizing agent(s) may be added in solid or liquid form at any process steps.

The method of adding the stabilizing agent(s) in solid form is not limited, and examples of the method include methods in which the commercially available stabilizing agent(s) is/are pulverized as necessary before mixing, and methods in which the stabilizing agent(s) suspended in water, an alcohol such as ethanol or methanol, or a mixed solution thereof is/are added.

The method of adding the stabilizing agent(s) in liquid form is not limited, and examples of the method include methods in which the stabilizing agent(s) and the active ingredient are together dissolved in water or a pharmaceutically acceptable solvent and then added to a carbohydrate, and methods in which the active ingredient is added to a carbohydrate, the resultant is then subjected to an appropriate granulation or size selection step, and the stabilizing agent(s) is/are subsequently added to the resulting granules. Additionally, the whole amount of the carbohydrate may be used at the above-described step of adding the active ingredient, or a partial amount of the carbohydrate may be used at the above-described step and the remaining amount of the carbohydrate may be added at any of the subsequent steps.

Commonly used apparatuses are used in the wet granulation process, including, for example, fluid bed granulator, tumbling fluid bed granulator, rotating granulator, cylindrical extrusion granulator, or wet-type extrusion granulator. When water is used as the solvent to dissolve or suspend the active ingredient, a fluid bed granulator or tumbling fluid bed granulator which is capable of spray drying is preferred. When a volatile solvent such as ethanol is used as the solvent to dissolve or suspend the active ingredient, a fluid bed granulator, tumbling fluid bed granulator, or rotating granulator is preferred.

When the stabilizing agent(s) in solid foam is/are added, a commonly used mixer is used, including, for example, V-type mixer, ribbon mixer, or air blender.

In addition, the addition of yellow ferric oxide, red ferric oxide, or black iron oxide as a coloring agent to the solid preparation can further improve the photostability of the solid preparation. The method of adding the coloring agent is not limited, and the coloring agent can be added in powder form or as a suspension in water or a pharmaceutically acceptable solvent.

When the solid preparation is in tablet form, commonly used apparatuses are used for compression molding, including, for example, single punch tableting machine or rotary tableting machine. The molding pressure during the compression process is not limited to a particular pressure as long as the resulting tablets are hard enough not to cause problems in handling.

The photostability of the active ingredient is improved in the solid preparation, which may thus be easily handled during drug preparation or drug dosing. The improved stability means that the above 4,5-epoxymorphinan derivative represented by general formula (I) or a pharmaceutically acceptable acid addition salt thereof is maintained in the preparation at a residual rate of not less than 90%, as described in WO 16/052617. The residual rate of the active ingredient is not less than 90% after period of at least 24 hours (an overall illumination of 48 thousand lux·hr), more preferably not less than 90% after a period of 300 hours (an overall illumination of 600 thousand lux·hr), when the solid preparation is handled at a temperature of 25° C. and a relative humidity of 51% RH under white fluorescent light (with an illumination of 2000 lux) without being packed.

EXAMPLES

Our solid preparations will be now described by way of examples to illustrate advantageous effects. However, this disclosure is not limited to the examples.

Comparative Example 1

Into a fluid bed granulator (LAB-1; manufactured by Powrex Corporation), mannitol (88.8975 parts by weight (hereinafter abbreviated to "parts" unless otherwise particularly stated) of PEARLITOL® 200SD; manufactured by Roquette Japan K.K.) was introduced and an aqueous solution of 0.0025 parts of nalfurafine hydrochloride was sprayed to produce granules. Then, those granules were mixed with 10 parts of low substituted hydroxypropyl cellulose (LH-11; manufactured by Shin-Etsu Chemical Co., Ltd.) and 1 part of magnesium stearate (manufactured by Taihei Chemical Industrial Co., Ltd.) to obtain granules for tablet compression. The granules for tablet compression were compressed using a tablet press (Correct 19; manufactured by Kikusui Seisakusho Ltd.) into tablets with a weight of 99.9 mg and a diameter of 7 mm.

Example 1

Into a fluid bed granulator (LAB-1; manufactured by Powrex Corporation), mannitol (88.8975 parts of PEARLI- TOL® 200SD; manufactured by Roquette Japan K.K.) was introduced and an aqueous solution of 0.0025 parts of nalfurafine hydrochloride was sprayed to produce granules, to which an ethanol solution of 0.1 parts of n-propyl gallate (Wako 1st Grade; manufactured by Wako Pure Chemical Industries, Ltd.) was added, and the resulting mixture was stirred in a mortar. After drying at 40° C. for 16 hours in a hot air dryer, the mixture was mixed with 10 parts of low substituted hydroxypropyl cellulose and 1 part of magnesium stearate to obtain granules for tablet compression. The granules for tablet compression were compressed using a tablet press into tablets with a weight of 100 mg and a diameter of 7 mm.

Example 2

Tablets with a weight of 100 mg and a diameter of 7 mm were obtained in the same manner as in Example 1, except that 0.1 parts of dl-α-tocopherol (Guaranteed Reagent; manufactured by Kanto Chemical Co., Inc.) were used instead of 0.1 parts of n-propyl gallate in Example 1.

Example 3

Tablets with a weight of 100 mg and a diameter of 7 mm were obtained in the same manner as in Example 1, except that 0.1 parts of 3-t-butyl-4-hydroxyanisole (BHA) (Extra Pure; manufactured by Nacalai Tesque, Inc.) were used instead of 0.1 parts of n-propyl gallate in Example 1.

Example 4

Tablets with a weight of 100 mg and a diameter of 7 mm were obtained in the same manner as in Example 1, except that 0.1 parts of 2,6-di-t-butyl-p-cresol (BHT) (Extra Pure Reagent; manufactured by Nacalai Tesque, Inc.) were used instead of 0.1 parts of n-propyl gallate in Example 1.

Example 5

Tablets with a weight of 100 mg and a diameter of 7 mm were obtained in the same manner as in Example 1, except that an aqueous solution of 0.1 parts of D-isoascorbic acid (Guaranteed Reagent; manufactured by Nacalai Tesque, Inc.) was used instead of the ethanol solution of 0.1 parts of n-propyl gallate in Example 1.

Example 6

Tablets with a weight of 100 mg and a diameter of 7 mm were obtained in the same manner as in Example 1, except that an aqueous solution of 0.1 parts of sodium sulfite (Guaranteed Reagent; manufactured by Wako Pure Chemical Industries, Ltd.) was used instead of the ethanol solution of 0.1 parts of n-propyl gallate in Example 1.

Comparative Example 2

Tablets with a weight of 100 mg and a diameter of 7 mm were obtained in the same manner as in Example 1, except that an aqueous solution of 0.1 parts of sodium thiosulfate pentahydrate (Guaranteed Reagent; manufactured by Kokusan Chemical Co., Ltd.) was used instead of the ethanol solution of 0.1 parts of n-propyl gallate in Example 1.

Comparative Example 3

Tablets with a weight of 100 mg and a diameter of 7 mm were obtained in the same manner as in Example 1, except that an aqueous solution of 0.1 parts of sodium hydrogensulfite (Guaranteed Reagent; manufactured by Wako Pure Chemical Industries, Ltd.) was used instead of the ethanol solution of 0.1 parts of n-propyl gallate in Example 1.

Test Example 1: Photostability Test on Tablets

The tablets of Examples 1 to 6 and Comparative Examples 1 to 3 were arranged on glass dishes such that no tablets piled upon each other, and the glass dishes were exposed under white fluorescent light (with an illumination of 2000 lux) to an overall illumination of 48 thousand lux·hr and to an overall illumination of 600 thousand lux·hr, and the tablets were then collected from the glass dishes. Additionally, glass dishes on which the tablets of Example 1 and Comparative Example 1 were arranged were covered with aluminium foil (for storage in the dark) and exposed to an overall illumination of 48 thousand lux·hr, and the tablets were then collected from the glass dishes. The tablets were analyzed by the following HPLC analysis to calculate the residual rates of the active ingredient.
Pretreatment Conditions
A mixed solution of 25 mM phosphate buffer and methanol (40/60; v/v) was added to the tablets to disintegrate the tablets, and the resulting mixture was stirred and then centrifuged to collect the supernatant as a HPLC sample.
HPLC Conditions
Mobile phase: 25 mM phosphate buffer (pH 7.0)/acetonitrile=60/40 (v/v);
Column: "Capcell Pak®" MGII (3.0×150 mm in size; manufactured by Shiseido Co., Ltd.);
Column temperature: 40° C.;
Detection wavelength: 280 nm;
Injection volume: 100 μL.
The residual rate of the active ingredient after exposure to light was calculated with Formula 1.

Residual rate (%)=(The area value of the HPLC peak of the active ingredient in the sample after exposure to light/the area value of the HPLC peak of the active ingredient in the sample before exposure to light)×100     Formula 1

The ingredients in the tablets of Examples 1 to 6 and Comparative Examples 1 to 3, the contents of the respective ingredients in percent by weight of each solid preparation, and the residual rates of the active ingredient after exposure to light obtained as the results of the HPLC analysis are shown in Table 1.

TABLE 1

| | | Comparative Example 1 Tablet | Comparative Example 2 Tablet | Comparative Example 3 Tablet | Example 1 Tablet | Example 2 Tablet | Example 3 Tablet | Example 4 Tablet | Example 5 Tablet | Example 6 Tablet |
|---|---|---|---|---|---|---|---|---|---|---|
| Active ingredient | Nalfurafine hydrochloride | 0.0025 | 0.0025 | 0.0025 | 0.0025 | 0.0025 | 0.0025 | 0.0025 | 0.0025 | 0.0025 |

TABLE 1-continued

| | | Comparative Example 1 Tablet | Comparative Example 2 Tablet | Comparative Example 3 Tablet | Example 1 Tablet | Example 2 Tablet | Example 3 Tablet | Example 4 Tablet | Example 5 Tablet | Example 6 Tablet |
|---|---|---|---|---|---|---|---|---|---|---|
| Carbohydrate | Mannitol | 88.9865 | 88.8975 | 88.8975 | 88.8975 | 88.8975 | 88.8975 | 88.8975 | 88.8975 | 88.8975 |
| Stabilizing agent | Sodium thiosulfate | | 0.1 | | | | | | | |
| | Sodium hydrogensulfite | | | 0.1 | | | | | | |
| | Propyl gallate | | | | 0.1 | | | | | |
| | Tocopherol | | | | | 0.1 | | | | |
| | BHA | | | | | | 0.1 | | | |
| | BHT | | | | | | | 0.1 | | |
| | Isoascorbic acid | | | | | | | | 0.1 | |
| | Sodium sulfite | | | | | | | | | 0.1 |
| Disintegrator | Low substituted hydroxypropyl cellulose | 10 | 10 | 10 | 10 | 10 | 10 | 10 | 10 | 10 |
| Lubricant | Magnesium stearate | 1 | 1 | 1 | 1 | 1 | 1 | 1 | 1 | 1 |
| Total | | 100 | 100 | 100 | 100 | 100 | 100 | 100 | 100 | 100 |
| The residual rates in samples exposed to 48 thousand lux · hr (%) | | 79.8 | 87.6 | 87.4 | 99.6 | 95.7 | 94.2 | 91.4 | 92.3 | 90.5 |
| The residual rates in samples exposed to 600 thousand lux · hr (%) | | 27.7 | 27.7 | 45.3 | 90.8 | 76.4 | 61.1 | 44.1 | 71.2 | 56.4 |

As shown in Table 1, the tablets of Examples 1 to 6 in which a particular stabilizing agent was added maintained the active ingredient at a residual rate of not less than 90% in the samples exposed to an overall illumination of 48 thousand lux·hr, indicating that the photostability was improved in those samples. The tablets of Example 1 in which n-propyl gallate was added as a stabilizing agent further indicated to maintain the active ingredient at a very high residual rate even in the sample exposed to an overall illumination of 600 thousand lux·hr. Additionally, the residual rate of the active ingredient stored in the dark was 99.4% in Example 1 and 102.1% in Comparative Example 1, indicating that the residual rate was not decreased depending on the temperature and humidity conditions.

Comparative Example 4

Into a fluid bed granulator, 88.5 parts of mannitol was introduced and an aqueous solution of 0.0025 parts of nalfurafine hydrochloride was sprayed to produce granules. Then, an ethanol solution of 0.001 parts of n-propyl gallate was added to the granules and the resulting mixture was stirred in a mortar. After drying at 40° C. for 6 hours in a hot air dryer, the mixture was mixed with 10 parts of low substituted hydroxypropyl cellulose and 1 part of magnesium stearate to obtain granules for tablet compression. The granules for tablet compression were compressed using a tablet press into tablets with a weight of 99.5 mg and a diameter of 7 mm.

Example 7

Tablets with a weight of 99.5 mg and a diameter of 7 mm were obtained in the same manner as in Comparative Example 4, except that an ethanol solution of 0.005 parts of n-propyl gallate instead of 0.001 parts of n-propyl gallate was added to the granules of Comparative Example 4.

Example 8

Tablets with a weight of 99.5 mg and a diameter of 7 mm were obtained in the same manner as in Comparative Example 4, except that an ethanol solution of 0.01 parts of n-propyl gallate instead of 0.001 parts of n-propyl gallate was added to the granules of Comparative Example 4.

Example 9

Tablets with a weight of 99.6 mg and a diameter of 7 mm were obtained in the same manner as in Comparative Example 4, except that an ethanol solution of 0.1 parts of n-propyl gallate instead of 0.001 parts of n-propyl gallate was added to the granules of Comparative Example 4.

Example 10

Tablets with a weight of 100.5 mg and a diameter of 7 mm were obtained in the same manner as in Comparative Example 4, except that an ethanol solution of 1.0 part of n-propyl gallate instead of 0.001 parts of n-propyl gallate was added to the granules of Comparative Example 4.

Example 11

Tablets with a weight of 104.5 mg and a diameter of 7 mm were obtained in the same manner as in Comparative Example 4, except that an ethanol solution of 5 parts of n-propyl gallate instead of 0.001 parts of n-propyl gallate was added to the granules of Comparative Example 4.

The photostability test described in Test Example 1 was performed on the tablets of Comparative Example 4 and Examples 7 to 11. The ingredients in the tablets of Comparative Examples 1 and 4 and Examples 7 to 11, the contents of the respective ingredients in percent by weight of each solid preparation, and the residual rates of the active ingredient after exposure to light obtained as the results of the HPLC analysis are shown in Table 2.

TABLE 2

| | | Comparative Example 1 Tablet | Comparative Example 4 Tablet | Example 7 Tablet | Example 8 Tablet | Example 9 Tablet | Example 10 Tablet | Example 11 Tablet |
|---|---|---|---|---|---|---|---|---|
| Active ingredient | Nalfurafine hydrochloride | 0.0025 | 0.0025 | 0.0025 | 0.0025 | 0.0025 | 0.0025 | 0.0024 |
| Carbohydrate | Mannitol | 88.9865 | 88.9447 | 88.9447 | 88.9447 | 88.8554 | 88.0597 | 84.6890 |
| Stabilizing agent | Propyl gallate | — | 0.001 | 0.005 | 0.01 | 0.1 | 1.0 | 4.8 |
| Disintegrator | Low substituted hydroxypropyl cellulose | 10 | 10 | 10 | 10 | 10 | 10 | 10 |
| Lubricant | Magnesium stearate | 1 | 1 | 1 | 1 | 1 | 1 | 1 |
| Total | | 100 | 100 | 100 | 100 | 100 | 100 | 100 |
| The residual rates in samples exposed to 48 thousand lux · hr (%) | | 79.8 | 89.7 | 96.4 | 96.4 | 97.3 | 99.0 | 98.2 |

As shown in Table 2, we found that the stabilizing agent at a dosage of 0.001% (Comparative Example 4) did not provide a sufficient photostabilizing effect and, meanwhile, the stabilizing agent at a dosage of 0.005 to 5% (Examples 7 to 11) contributed to the production of solid preparations with significantly improved photostability.

Example 12

To the granules of Comparative Example 4, 1.0 part of n-propyl gallate was added, and the resulting mixture was mixed with 10 parts of low substituted hydroxypropyl cellulose and 1 part of magnesium stearate to obtain granules for tablet compression. The granules for tablet compression were compressed using a tablet press into tablets with a weight of 100.5 mg and a diameter of 7 mm.

Example 13

Into a fluid bed granulator, 88.5 parts of mannitol was introduced and a solution containing two solutes, which were 0.0025 parts of nalfurafine hydrochloride and 0.1 parts of n-propyl gallate, in 30% ethanol was sprayed to produce granules.

Example 14

The granules obtained in Example 13 were mixed with 10 parts of low substituted hydroxypropyl cellulose and 1 part of magnesium stearate to obtain granules for tablet compression. The granules for tablet compression were compressed using a tablet press into tablets with a weight of 99.5 mg and a diameter of 7 mm.

Example 15

Into a fluid bed granulator, 88.5 parts of mannitol was introduced and an aqueous solution containing two solutes, which were 0.0025 parts of nalfurafine hydrochloride and 0.1 parts of sodium thiosulfate pentahydrate, was sprayed to produce granules. Then, an ethanol solution of 0.1 parts of n-propyl gallate was added to the granules and the resulting mixture was stirred in a mortar. After drying at 40° C. for 6 hours in a hot air dryer, the mixture was mixed with 10 parts of low substituted hydroxypropyl cellulose and 1 part of magnesium stearate to obtain granules for tablet compression. The granules for tablet compression were compressed using a tablet press into tablets with a weight of 99.7 mg and a diameter of 7 mm.

Example 16

Tablets with a weight of 100.1 mg and a diameter of 7 mm were obtained in the same manner as in Example 15, except that an ethanol solution of 0.5 parts of n-propyl gallate instead of 0.1 parts of n-propyl gallate was added to the granules of Example 15.

Example 17

Tablets with a weight of 100.6 mg and a diameter of 7 mm were obtained in the same manner as in Example 15, except that an ethanol solution of 1 part of n-propyl gallate instead of 0.1 parts of n-propyl gallate was added to the granules of Example 15.

Example 18

Into a fluid bed granulator, 88.5 parts of mannitol was introduced and a solution containing three solutes, which were 0.0025 parts of nalfurafine hydrochloride, 0.1 parts of sodium thiosulfate pentahydrate and 0.1 parts of n-propyl gallate, in 30% ethanol was sprayed to produce granules.

Example 19

The granules of Example 18 were mixed with 10 parts of low substituted hydroxypropyl cellulose and 1 part of magnesium stearate to obtain granules for tablet compression. The granules for tablet compression were compressed using a tablet press into tablets with a weight of 99.7 mg and a diameter of 7 mm.

Test Example 2: Test to Determine the Ratio of the Generated Main Degradation Product a to the Active Ingredient During the Production The granules of Examples 13 and 18 were further air-dried for 30 minutes, and the resulting powders were analyzed by the following HPLC analysis to calculate the ratios of the generated main degradation product A to the active ingredient.

Pretreatment Conditions

Methanol was added to the powder, and the resulting mixture was stirred and then centrifuged to collect the supernatant. The collected solution was concentrated to a solid with a rotary evaporator and the resulting solid was then redissolved with the mobile phase A to prepare an HPLC sample.

HPLC Conditions

Mobile phase A: 50 mM sodium dihydrogen phosphate solution/acetonitrile=95/5 (v/v);
Mobile phase B: 50 mM sodium dihydrogen phosphate solution/acetonitrile=60/40 (v/v);
Column: YMC-Pack ODS-AM (4.×250 mm in size; manufactured by YMC Co., Ltd.);
Column temperature: 40° C.;
Detection wavelength: 280 nm;
Flow rate: 1.0 ml/min.

The production ratio of the main degradation product A was calculated with Formula 2.

Production ratio (%)=(The area value of the HPLC peak of the main degradation product A in the sample/the area value of the peak of the active ingredient in the sample)×100    Formula 2

The production ratios of the main degradation product A in the granules of Examples 13 and 18 immediately after the production of those granules are shown in Table 3.

TABLE 3

|  |  | Example 13 Powder | Example 18 Powder |
|---|---|---|---|
| Active ingredient | Nalfurafine hydrochloride | 0.0028 | 0.0028 |
| Carbohydrate | Mannitol | 99.8843 | 99.7717 |
| Stabilizing agent | Propyl gallate | 0.11 | 0.11 |
| Antioxidant | Sodium thiosulfate | — | 0.11 |
| Total |  | 100 | 100 |
| The production ratios of the main degradation product A in air-dried samples (%) |  | 1.24 | 0.38 |

As shown in Table 3, a significant reduction in the ratio of the main degradation product during the production was indicated in the granules of Example 18 to which sodium thiosulfate, which is an antioxidant, was further added, as compared to those of Example 13.

The photostability test described in Test Example 1 was performed on the tablets of Example 12, Examples 14 to 17 and Example 19. The ingredients in the tablets of Example 12, Examples 14 to 17 and Example 19, the contents of the respective ingredients in percent by weight of each solid preparation, and the residual rates of the active ingredient after exposure to light obtained as the results of the HPLC analysis are shown in Table 4.

As shown in Table 4, the stabilizing agent exhibited an excellent photostabilizing effect even when the stabilizing agent was added in powder form (Example 12). Additionally, the improvement of photostability was indicated even when the stabilizing agent was sprayed together with the active ingredient (Example 14). In addition, the photostabilizing effect was maintained even when sodium thiosulfate, which is an antioxidant, was used in combination with the stabilizing agent, indicating that an excellent stabilizing effect was obtained irrespective of the way of adding the stabilizing agent and sodium thiosulfate.

Comparative Example 5

Granules described in WO 99/002158 were produced as follows. In a mortar, 68.9 parts of lactose (Pharmatose® 200M) and 31 parts of crystalline cellulose (CEOLUS® PH-101; manufactured by Asahi Kasei Chemicals Corporation) were placed, and an aqueous solution of 0.1 parts of nalfurafine hydrochloride was added thereto, and the resulting mixture was stirred. Then, the mixture was dried at 40° C. for 12 hours to produce granules.

Comparative Example 6

Granules described in WO 99/002158 were produced as follows. In a mortar, 68.8 parts of lactose (Pharmatose® 200M) and 31 parts of crystalline cellulose (CEOLUS® PH-101; manufactured by Asahi Kasei Chemicals Corporation) were placed, and an aqueous solution containing two solutes, which were 0.1 parts of nalfurafine hydrochloride and 0.1 parts of sodium thiosulfate, was added thereto, and the resulting mixture was stirred. Then, the mixture was dried at 40° C. for 12 hours to produce granules.

Comparative Example 7

In a mortar, 99.95 parts of mannitol was placed, and an aqueous solution of 0.05 parts of nalfurafine hydrochloride was added thereto, and the resulting mixture was stirred. Then, the mixture was dried at 40° C. for 12 hours to produce granules.

Comparative Example 8

In a mortar, 99.99 parts of mannitol was placed, and an aqueous solution of 0.01 parts of nalfurafine hydrochloride was added thereto, and the resulting mixture was stirred. Then, the mixture was dried at 40° C. for 12 hours to produce granules.

TABLE 4

|  |  | Example 12 Tablet | Example 14 Tablet | Example 15 Tablet | Example 16 Tablet | Example 17 Tablet | Example 19 Tablet |
|---|---|---|---|---|---|---|---|
| Active ingredient | Nalfurafine hydrochloride | 0.0025 | 0.0025 | 0.0025 | 0.0025 | 0.0025 | 0.0025 |
| Carbohydrate | Mannitol | 88.0597 | 88.9447 | 88.7663 | 88.4116 | 87.9722 | 88.7663 |
| Stabilizing agent | Propyl gallate | 1.0 | 0.1 | 0.1 | 0.5 | 1.0 | 0.1 |
| Antioxidant | Sodium thiosulfate | — | — | 0.1 | 0.1 | 0.1 | 0.1 |
| Disintegrator | Low substituted hydroxypropyl cellulose | 10 | 10 | 10 | 10 | 10 | 10 |
| Lubricant | Magnesium stearate | 1 | 1 | 1 | 1 | 1 | 1 |
| Total |  | 100 | 100 | 100 | 100 | 100 | 100 |
| The residual rates in samples exposed to 48 thousand lux · hr (%) |  | 97.3 | 98.3 | 97.7 | 99.6 | 100.4 | 102.7 |

Example 20

In a mortar, 99.89 parts of mannitol was placed, and an aqueous solution of 0.01 parts of nalfurafine hydrochloride was added thereto with stirring, and an ethanol solution of 0.1 parts of n-propyl gallate was then added thereto, and the resulting mixture was stirred. Then, the mixture was dried at 40° C. for 12 hours to produce granules.

Example 21

Into a fluid bed granulator, 88.5 parts of mannitol was introduced and a solution containing three solutes, which were 0.0025 parts of nalfurafine hydrochloride, 0.1 parts of sodium thiosulfate and 0.1 parts of n-propyl gallate, in 30% ethanol was sprayed to produce granules. Then, 455.65 parts of mannitol was added to 44.35 parts of the granules, and the resulting mixture was mixed using a V-type mixer.

Test Example 3: Photostability Test on Powders

The powders of Comparative Examples 5 to 8 and Examples 20 and 21 were spread thinly on glass dishes, and the glass dishes were exposed under white fluorescent light (with an illumination of 2000 lux) to an overall illumination of 48 thousand lux·hr, and the powders were then collected from the glass dishes, and the powders were analyzed by the following HPLC analysis to calculate the residual rates of the active ingredient after exposure to light by the same formula as Formula 1.
Pretreatment Conditions Distilled water was added to the powder to suspend or dissolve the powder, and the resulting mixture was centrifuged to collect the supernatant as an HPLC sample.
HPLC Conditions The test was performed under the same HPLC conditions as those in Test Example 1.

The photostability test described in Test Example 2 was performed on the powders of Comparative Examples 5 to 8 and Examples 20 and 21. The ingredients in the powders of Comparative Examples 5 to 8 and Examples 20 and 21, the contents of the respective ingredients in percent by weight of each solid preparation, and the residual rates of the active ingredient after exposure to light obtained as the results of the HPLC analysis are shown in Table 5.

As shown in Table 5, the solid preparations containing the active ingredient at a concentration of 0.1% by weight according to WO 99/002158 (Comparative Examples 5 and 6) and the solid preparation containing the active ingredient at a concentration of 0.05% by weight (Comparative Example 7) ensured photostability without any added stabilizing agent, indicating that the known problems are particularly relevant to solid preparations with a low content of nalfurafine. Additionally, the desired effect was shown even in a solid preparation containing the active ingredient at a concentration of 0.00025% by weight.

Comparative Example 9

Vanillin, which is a light absorbing agent described in JP S58-57322 A, was used. In a mortar, 99.8975 parts of mannitol was placed, and an aqueous solution of 0.0025 parts of nalfurafine hydrochloride was added thereto and the resultant was stirred. Thereafter, an ethanol solution of 0.1 parts of vanillin (Guaranteed Reagent; manufactured by Wako Pure Chemical Industries, Ltd.) was added to the resultant, and the resulting mixture was stirred. The mixture was then dried at 40° C. for 12 hours to produce granules.

Comparative Example 10 p-Aminobenzoic acid (Guaranteed Reagent; manufactured by Wako Pure Chemical Industries, Ltd.), which is a light absorbing agent described in JP S58-57322 A, was used. In a mortar, 99.8975 parts of mannitol was placed, and an aqueous solution of 0.0025 parts of nalfurafine hydrochloride was added thereto and the resultant was stirred. Thereafter, an ethanol solution of 0.1 parts of p-aminobenzoic acid was added to the resultant, and the resulting mixture was stirred. The mixture was then dried at 40° C. for 12 hours to produce granules.

Example 22

In a mortar, 99.7975 parts of mannitol was placed, and an aqueous solution of 0.0025 parts of nalfurafine hydrochloride was added thereto, and the resultant was stirred. To the mortar, 0.1 parts of ferric oxide (Sicovit Red 30E172; manufactured by Huntsman Corporation) was added, and an ethanol solution of 0.1 parts of n-propyl gallate was then added thereto, and the resulting mixture was stirred. Then, the mixture was dried at 40° C. for 12 hours to produce granules.

TABLE 5

|  |  | Comparative Example 5 Powder | Comparative Example 6 Powder | Comparative Example 7 Powder | Comparative Example 8 Powder | Example 20 Powder | Example 21 Powder |
|---|---|---|---|---|---|---|---|
| Active ingredient | Nalfurafine hydrochloride | 0.1 | 0.1 | 0.05 | 0.01 | 0.01 | 0.00025 |
| Excipient | Crystalline cellulose | 31 | 31 |  |  |  |  |
| Carbohydrate | Lactose | 68.9000 | 68.8000 |  |  |  |  |
| Carbohydrate | Mannitol |  |  | 99.9500 | 99.9900 | 99.8900 | 99.9798 |
| Stabilizing agent | Propyl gallate |  |  |  |  | 0.1 | 0.01 |
| Antioxidant | Sodium thiosulfate |  | 0.1 |  |  |  | 0.01 |
| Total |  | 100 | 100 | 100 | 100 | 100 | 100 |
| The residual rates in samples exposed to 48 thousand lux · hr (%) |  | 102.9 | 97.6 | 93.9 | 75.4 | 100.8 | 95.1 |

Example 23

In a mortar, 100 parts of the granules of Example 21 were placed, and 0.01 parts of ferric oxide and an aqueous ethanol solution were added thereto, and the resulting mixture was stirred. Then, the mixture was dried for 12 hours to produce granules.

The photostability test described in Test Example 2 was performed on the powders of Comparative Examples 9 and 10 and Examples 22 and 23. The ingredients in the powders of Comparative Examples 9 and 10 and Examples 22 and 23, the contents of the respective ingredients in percent by weight of each solid preparation, and the residual rates of the active ingredient after exposure to light obtained as the results of the HPLC analysis are shown in Table 6.

TABLE 6

|  |  | Comparative Example 9 Powder | Comparative Example 10 Powder | Example 22 Powder | Example 23 Powder |
|---|---|---|---|---|---|
| Active ingredient | Nalfurafine hydrochloride | 0.0025 | 0.0025 | 0.0025 | 0.00025 |
| Carbohydrate | Mannitol | 99.8975 | 99.8975 | 99.7975 | 99.9698 |
| Additives | Vanillin | 0.1 | | | |
| Additives | p-aminobenzoic acid | | 0.1 | | |
| Stabilizing agent | Propyl gallate | | | 0.1 | 0.01 |
| Antioxidant | Sodium thiosulfate | | | | 0.01 |
| Coloring agent | Ferric oxide | | | 0.1 | 0.01 |
|  | Total | 100 | 100 | 100 | 100 |
| The residual rates in samples exposed to 48 thousand lux · hr (%) |  | 79.9 | 89.2 | 100.0 | 100.9 |

As shown in Table 6, vanillin and p-aminobenzoic acid, which are light absorbing agents described in JP S58-57322 A, provided an insufficient photostabilizing effect to the active ingredient, which is the above 4,5-epoxymorphinan derivative represented by general formula (I) or a pharmaceutically acceptable acid addition salt thereof, indicating that different stabilization methods are effective for different active ingredients. Additionally, we found that the photostabilizing effect was further enhanced by the addition of ferric oxide as a coloring agent as well as the stabilizing agent, as shown in Example 22. In addition, we found that the photostability of the active ingredient was improved as shown in Example 23 even when ferric oxide was added at a dosage of 0.01% of the solid preparation, which is smaller than the dosage of ferric oxide relative to the composition according to JP 2006-306754 A, namely 0.1%.

INDUSTRIAL APPLICABILITY

The photostability of a solid preparation containing a 4,5-epoxymorphinan derivative or a pharmaceutically acceptable acid addition salt thereof is improved, which greatly improves the convenience in handling the solid preparation in split tablets or in powder, which has been difficult so far and, consequently, reduces the risk of pharmacy compounding errors, improves the drug compliance in patients, and enhances the therapeutic effect of the solid preparation. Moreover, the solid preparation is stable to light even without light shielding coating, which contributes to simplifying the production process and allows tablets to ensure rapid disintegration properties.

The invention claimed is:

1. A solid preparation comprising an active ingredient composed of a 4,5-epoxymorphinan derivative represented by general formula (I) or a pharmaceutically acceptable acid addition salt thereof, and n-propyl gallate, wherein an amount of the active ingredient is 0.00025 to 0.01% by weight of the solid preparation, wherein an amount of the n-propyl gallate is 0.005 to 1% by weight of the solid preparation, and wherein the solid preparation is in a dosage form selected from the group consisting of tablet, granule, dry syrup, powder, pill and troche,

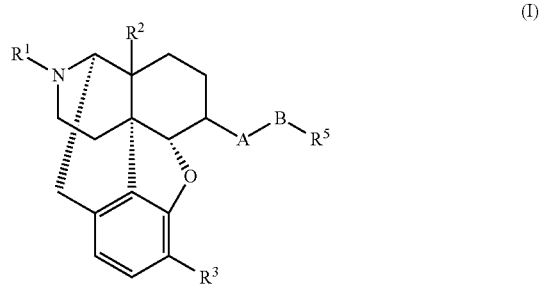

(I)

wherein $R^1$ represents cyclopropylmethyl or allyl; $R^2$ represents hydrogen, hydroxy, acetoxy, or methoxy; $R^3$ represents hydrogen, hydroxy, acetoxy, or methoxy; A represents —N($R^4$)C(=O)— or —N($R^4$)C(=O)O—; $R^4$ represents hydrogen or a $C_{1-5}$ linear or branched alkyl; B represents a $C_{1-3}$ linear alkylene, —CH=CH—, or —C≡C—; $R^5$ represents hydrogen, phenyl, furyl, or thienyl, provided that a hydrogen(s) in the phenyl, the furyl and the thienyl is/are optionally substituted with one or more groups selected from the group consisting of $C_{1-5}$ alkyl, $C_{1-5}$ alkoxy, $C_{1-5}$ alkanoyloxy, hydroxy, fluorine, chlorine, bromine, iodine, amino, nitro, cyano, isothiocyanato, trifluoromethyl, trifluoromethoxy and methylenedioxy.

2. The solid preparation according to claim 1, further containing sodium thiosulfate.

3. The solid preparation according to claim 1, further containing yellow ferric oxide, red ferric oxide, or black iron oxide.

4. The solid preparation according to claim 1, further containing a carbohydrate.

5. The solid preparation according to claim 2, further containing yellow ferric oxide, red ferric oxide, or black iron oxide.

6. The solid preparation according to claim 2, further containing a carbohydrate.

* * * * *